United States Patent
Prueter

(10) Patent No.: US 6,250,568 B1
(45) Date of Patent: Jun. 26, 2001

(54) SQUEEZE BOTTLE ASPIRATOR

(75) Inventor: David M. Prueter, Lenexa, KS (US)

(73) Assignee: Saint-Gobain Calmar Inc., City of Industry, CA (US)

( * ) Notice: Subject to any disclaimer, the term of this patent is extended or adjusted under 35 U.S.C. 154(b) by 0 days.

(21) Appl. No.: 09/533,166

(22) Filed: Mar. 22, 2000

(51) Int. Cl.[7] .................................................. A61M 11/02
(52) U.S. Cl. ........................ 239/371; 239/327; 239/372; 239/288.5; 222/211
(58) Field of Search .................................. 239/327, 372, 239/369, 371, 288, 288.3, 288.5; 222/207, 211, 212, 631, 632, 633; 215/276, 274

(56) References Cited

U.S. PATENT DOCUMENTS

| | | |
|---|---|---|
| 2,823,836 * | 2/1958 | Bach . |
| 3,439,843 * | 4/1969 | Corsette . |
| 3,710,989 * | 1/1973 | Armour . |
| 4,007,857 * | 2/1977 | Tomiati et al. ................. 222/153.14 |
| 4,122,979 | 10/1978 | Laauwe . |
| 4,157,789 | 6/1979 | Laauwe . |
| 4,186,882 * | 2/1980 | Szczepanski . |
| 4,244,495 | 1/1981 | Lorscheid et al. . |
| 4,253,609 | 3/1981 | Laauwe . |
| 4,415,122 | 11/1983 | Laauwe . |
| 4,673,110 | 6/1987 | Workum . |
| 4,773,570 * | 9/1988 | Workum ................................ 222/211 |
| 5,183,186 | 2/1993 | Delaney, Jr. . |
| 5,318,205 | 6/1994 | Delaney, Jr. . |
| 5,409,136 | 4/1995 | Workum . |
| 5,462,181 * | 10/1995 | Glynn . |
| 5,735,464 * | 4/1998 | Darrach, III ....................... 239/288.5 |
| 6,062,436 * | 5/2000 | Fuchs .................................... 222/212 |

* cited by examiner

Primary Examiner—David A. Scherbel
Assistant Examiner—Christopher S. Kim
(74) Attorney, Agent, or Firm—Dykema Gossett PLLC

(57) ABSTRACT

A squeeze bottle atomizer comprised of a tube retainer having a product outlet port in a conical shaped central post through which fluid is expelled from within the container. A plurality of air inlet ports are located adjacent the central post and allow air to be forced and sucked out of the post when squeezed as well as return and be sucked into the interior of the container when the container is released. The orifice cup has an annular mixing or turbulence chamber wherein the air and the fluid from within the container are mixed before being expelled out of the orifice cup through a discharge orifice. The axis of the product outlet port is coincident with the axis of the discharge orifice. A dip tube depends from the tube retainer and defines a path for the fluid from the bottom of the container to the annular mixing chamber.

5 Claims, 1 Drawing Sheet

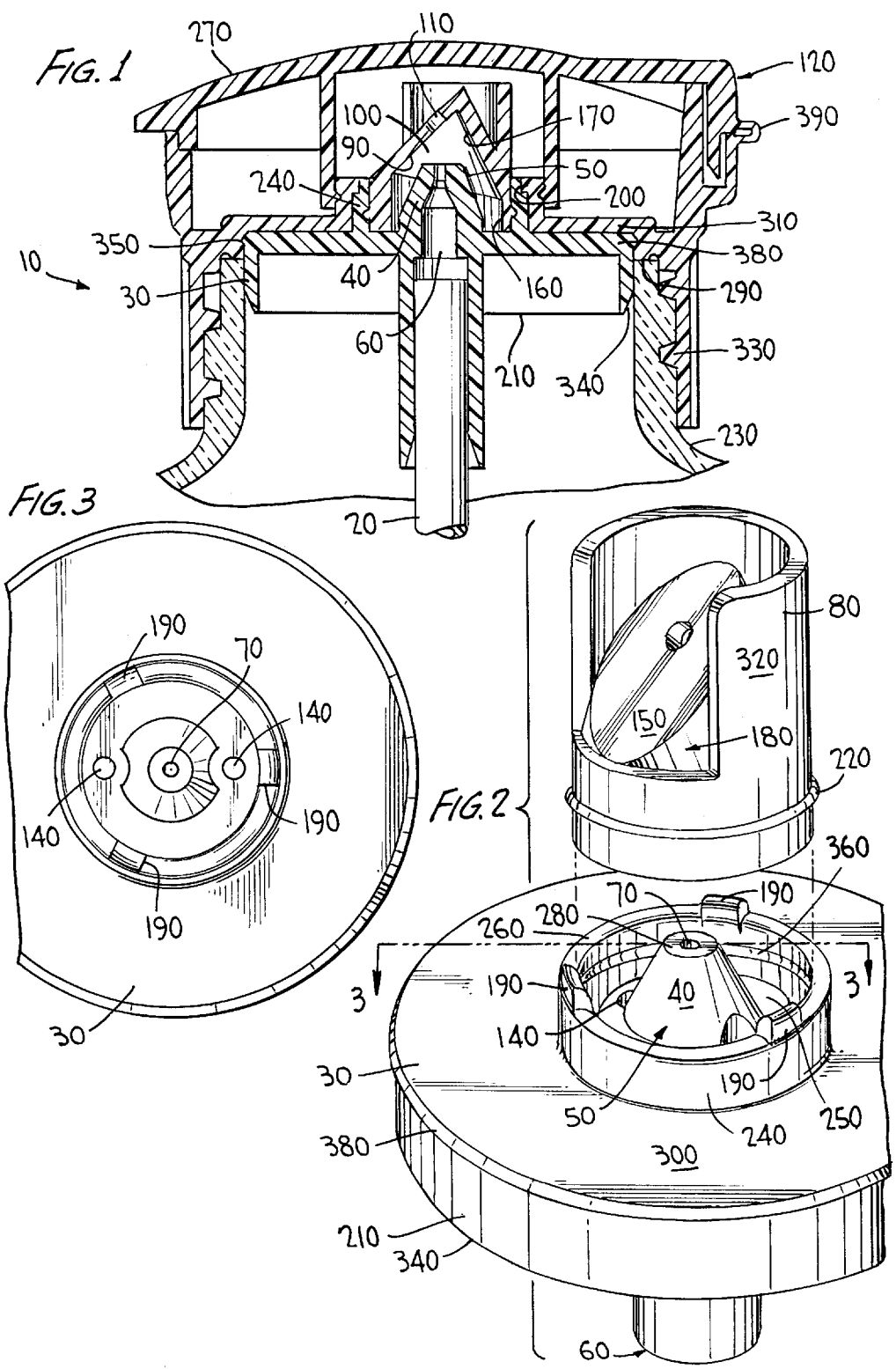

SQUEEZE BOTTLE ASPIRATOR

BACKGROUND OF THE INVENTION

This invention relates generally to a hand operable atomizer and more particularly to a squeeze bottle aspirator having a spraying device that is highly efficient at atomizing and dispensing material from the squeeze bottle.

There is a need for a spraying device that generates consistent dispensing performance through the evacuation of substantially all the material in a container.

A common solution in the market today is to manufacture aspirators of two piece construction. They generally have a dispensing closure that incorporates a dip tube which allows fluid to be conveyed from the lower extremities of the bottle when the bottle is squeezed. The dispensing closure has an exit orifice molded therein. The dip tube is attached to the dispensing closure in a cylindrical attachment port on the side facing the interior of the bottle. The cylindrical port has a plurality of thin ribs spaced radially and extending axially along its inside diameter. When the dip tube is inserted into the cylindrical port, the ribs in conjunction with the outside diameter of the dip tube create gaps or channels between the inner diameter of the cylindrical port and the outside diameter of the dip tube. These channels allow air to be forced into the fluid stream as the bottle is squeezed. The air is entrained into the fluid flow causing extreme turbulence of the fluid as it mixes and issues the exit orifice of the closure.

Drawbacks to this solution are that since the turbulence generates very fine atomized fluid only, the performance of these systems is limited to short bursts of atomized fluid and the dispensing performance degrades very quickly due to the high air flow volume.

A common mechanism used in the art to mix air and fluid is spin mechanics. Some of the devices currently in the art that employ spin mechanics are disclosed in U.S. Pat. Nos. 4,157,789 and 4,253,609 issued to Laauwe. While the devices disclosed in these patents are directed to different types of spraying devices, various improvements are desirable to optimize the spray operation and the spray quality.

SUMMARY OF THE INVENTION

It is an object of the present invention to provide a sprayer that can accurately control the optimal air flow and liquid volume while also providing consistent dispensing performance.

The present invention may also be used with squeeze bottles currently known in the art, rendering the sprayer economical as well as easy to use.

According to the present invention, the spraying device is comprised of a protective closure having a lid that can be opened when the squeeze bottle aspirator is in use. The closure is connected to a container and supports a tube retainer that has an orifice cup fitted therewith. The tube retainer has a product outlet port in a central post through which fluid is expelled from within the container and a plurality of air inlet ports are located adjacent the product outlet port. These air inlet ports are provided to allow air to be forced out of the container when squeezed and they allow air to be introduced or sucked into the container when the manually applied squeeze pressure is released. The orifice cup has an annular mixing chamber wherein the air and the fluid from within the container are mixed before being expelled out of the orifice cup through a discharge orifice. A dip tube is connected to the tube retainer and is used to draw up fluid from the bottom of the container. The present invention also has a means for preventing relative rotation between the closure and the tube retainer that is comprised of a plurality of lugs located on the tube retainer that matingly fit within corresponding slots on the closure. Also provided is a single locking lug for orienting the orifice cup relative to the tube retainer. This assures the direction of the discharged fluid mixture to be opposite and away from the hinged end of the closure lid.

Other objects, advantages and novel features of the invention will become more apparent from the following detailed description of the invention when taken in conjunction with the accompanying drawings.

BRIEF DESCRIPTION OF THE DRAWINGS

FIG. 1 is a partial cross-sectional view of the squeeze bottle aspirator of the present invention, the aspirator is mounted on a squeeze bottle and has a closure attached thereto;

FIG. 2 is a partial exploded perspective view of the orifice cup and tube retainer portions of the aspirator of FIG. 1; and FIG. 3 is a partial top plan view of the tube retainer portion of the aspirator of the present invention.

DETAILED DESCRIPTION OF THE INVENTION

Referring to FIGS. 1 and 2, the squeeze bottle aspirator 10 is comprised of a closure generally designated 120, shown in a closed position, connected to a container 230 and supporting a tube retainer 30. The lower portion 30 of the closure 120 may be mounted to the upper end of the container 230 while the lid portion 270 of the closure 120 is used as a protective cover that can be opened when the container 230 is in use. Container 230 typically has a collapsible wall or collapsible wall portion to facilitate manual squeezing. Closure 120 includes an integral plug seal 290 or the like for fluid tightly sealing the tube retainer and closure to the container without the need for a sealing gasket.

The tube retainer 30, as shown in FIG. 2, is comprised of a top 300 having a skirt 210 depending downwardly from the outer edge of the top 300. The lower end 340 of the skirt 210 is chamfered to allow the tube retainer 30 to be easily inserted into the container 230. A lip 380 is formed on the upper end of the skirt 210 which matingly corresponds to a channel 350 in the intermediate portion 310 of the closure 120. When assembled, the lip 380 is snapped into place within the channel 350 thereby securing the tube retainer 30 within the closure 120.

A central wall 240 is located in the middle portion of the top 300 of the tube retainer 30 and defines a central area 250 which encircles a frusto-conically shaped post 40 located centrally therein. An interior groove 360 is formed on the interior of the central wall 240. The interior groove 360 is capable of receiving a corresponding bead 220 located on the orifice cup of the device to help maintain the orifice cup adjacent the tube retainer 30 and ensure air tight assembly of the various parts.

The post 40 is frusto-conical in shape and comprises an outer surface 50 with a product outlet port 70 located in the top portion 280 of the post 40, port 70 thus being coaxial with the conically shaped outer surface 50 of post 40. Within the post 40 is formed a product passage 60 which is in communication with a dip tube 20. The product passage 60 extends from a point within the container 230 and terminates in the product outlet port 70 in the top portion 280 of the post 40. The dip tube 20 is adapted to extend into a liquid product (not shown) in the container 230 with one end located near the bottom of the container 230 and the other end communicating with the product passage 60 thus providing a pathway for the fluid to travel from the bottom of the container 230 up and into a mixing chamber 100. The dip tube 20 allows product to be expelled easily from within the container 230 to the mixing chamber 100 regardless of how much product is present in the container 230.

A plurality of lugs 190 are spaced equidistantly around the upper rim 260 of the central wall 240 and correspond to slots in the intermediate portion 310 of the closure 120 to prevent relative rotation between the closure 120 and the tube retainer 30.

An orifice cup 80 is supported by the tube retainer 30 and is comprised of a lower, cylindrical portion 160 and an upper, conical portion 170 and having an inner wall 90. The inner wall 90 and conical portion 170 are spaced from the outer surface 50 of the post 40 to define chamber 100 therebetween. During operation of the aspirator, to be more fully described hereafter, fluid from within the container 230 can be forced into the mixing chamber 100 along with air that is forced into the mixing chamber 100 thereby creating a turbulence that mixes the air and fluid together.

The orifice cup 80 is comprised of a sloping wall 150 partially encircled by an outer wall 320. The outer wall 320 has an opening therein allowing for spray to exit the discharge orifice unobstructed. The outer wall 320 is used during assembly of the device and allows for the orifice cup 80 to be pushed into or forced down into the tube retainer 30 so that it is attached to the tube retainer 30 without damaging the sloping wall 150. The sloping wall 150 has an annular bead 220 located on its exterior surface which corresponds with the interior groove 360 within the central wall 240 of the tube retainer 30. When the orifice cup 80 is attached to the tube retainer 30, the annular bead 220 matingly fits within the interior groove 360 and helps to maintain the orifice cup 80 within the central wall 240. The sloping wall 150 has a discharge orifice 110 formed therein and spaced from the product outlet port 70 of the post 40. The axis of the product outlet port 70 is coincident with the axis of the discharge orifice 110. The sloping nature of the sloping wall 150 allows the air/fluid mixture from within the mixing chamber 100 to be expelled out through the discharge orifice 110 in a predetermined or desired direction, such as at a predetermined angle from the vertical.

A plurality of passages or air inlet ports 140 are formed in the tube retainer 30 providing communication between the mixing chamber 100 and the interior of the container 230. As shown in FIG. 3, the air inlet ports 140 are located on opposite sides of the post 40 and may accommodate the flow of air into and out of the container 230.

To operate the squeeze bottle aspirator 10 of the present invention, the user grasps the container 230 in one hand and squeezes the container 230 between the thumb and fingers forcing fluid from the bottom of the interior of the container 230 up through the dip tube 20 and into the mixing chamber 100 where it is mixed with air that is forced and sucked from the container 230 also into the mixing chamber 100. The aspirated air and fluid simultaneously enter the mixing chamber 100 wherein the conical shape of the post 40 focuses the air on the liquid emerging from the product outlet port 70 permitting the air and liquid to be intimately mixed together prior to exiting the mixing chamber 100 from the discharge orifice 110 in the form of an atomized spray. The air-to-fluid ratios can be controlled by varying the size of the air inlet ports 140 and the product outlet port 70. If the air inlet ports 140 are eliminated completely or are small, a coarsely atomized fluid is expelled from the squeeze bottle, while on the other hand, if large air inlet ports 140 are used, the fluid can be finely atomized. Once the air and fluid are mixed, the mixture is expelled from the mixing chamber 100 through the discharge orifice 110 located in the sloping wall 150 of the orifice cup 80 out into the atmosphere or onto a target surface. Particle size can also be controlled by the size of the discharge orifice.

As known in the art, compression of the container creates the discharge process whereas releasing of the compressed container allows air to be sucked into the container 230 from the atmosphere, through the discharge orifice 110 and into the annular mixing chamber 100 where it is then dispersed through the air inlet ports 140 to the interior of the container 230 for refilling the upper portion of the container 230 with air as in the normal manner.

Although particular embodiments of the invention have been described in detail herein with reference to the accompanying drawings, it is to be understood that the invention is not limited to those precise embodiments, and that various changes and modifications are possible. Some foreseeable alternative embodiments may include a three piece construction instead of the four piece embodiment herein illustrated. The three piece construction would be similar to the present embodiment with the closure and the tube retainer being a single, unitary piece instead of two separate elements. Also, while the present embodiment shows the lid 270 connected to the closure 120 at location 390 as a live hinge, the lid 270 does not form any part of the claimed invention and various other types of hinges or attachments may be used. Also, the aspirator need not have a lid 270 or the like attached thereto at all. Such changes and modifications may be effected by one skilled in the art without departing from the scope or spirit of the invention as defined in the appended claims.

What is claimed is:

1. A spraying device for squeeze bottles, comprising:

a dip tube adapted to be disposed within a product in a squeeze bottle;

a tube retainer for supporting said dip tube, said tube retainer including an integral post having a conically shaped outer surface, said post having a product passage formed therein, said passage communicating with said dip tube and said passage terminating in a product outlet port coaxial with the conically shaped outer surface;

a separate orifice cup mounted to said tube retainer, said orifice cup having an inner wall defining a cavity therewithin, said inner wall being spaced from said outer surface of said post to define therebetween an mixing chamber, said orifice cup having a wall containing a discharge orifice spaced from said product outlet port;

said product outlet port and said discharge orifice having central axes which intersect;

a closure adapted to be connected to the squeeze bottle; said tube retainer being mounted to said closure; and said tube retainer including an integral top wall containing passage means providing communication between said mixing chamber and an area beneath said tube retainer, said passage means being adjacent said post;

whereby upon manually squeezing the bottle, air from within said area beneath said tube retainer is drawn up through said passage means and is focused by the conical shape of said post on the liquid emerging from said product outlet port wherein the air intimately mixes with the product as it exits said product outlet port into said mixing chamber, the mixture is then expelled from said mixing chamber through said discharge orifice.

2. The sprayer device according to claim 1, wherein:

said wall containing the discharge orifice lies at a predetermined angle to the central axis of the product outlet port to cause a spray to be discharged from said annular mixing chamber in a predetermined direction.

3. The sprayer device according to claim 2, wherein:

said tube retainer has spaced, upwardly extending lugs thereon; and said closure having slots formed therein for receiving said lugs to prevent relative rotation between said tube retainer and said closure.

4. The sprayer device according to claim 3, wherein:

said orifice cup includes an upwardly extending cylindrical outer wall having an opening formed therein adjacent said discharge orifice providing access to said sloping wall.

5. The sprayer device according to claim 4, wherein:

said passage means comprises a pair of air inlet ports opening into said mixing chamber, said air inlet ports located on opposite sides of said post.

* * * * *